United States Patent [19]

Burkardt et al.

[11] Patent Number: 5,096,062

[45] Date of Patent: Mar. 17, 1992

[54] TRANSPORT SYSTEM FOR SHIPPING MICROBIOLOGICAL SAMPLES

[75] Inventors: Hans-Joachim Burkardt; Wilhelm Weber, both of Grenzach-Wyhlen, Fed. Rep. of Germany

[73] Assignee: Hoffmann-La Roche Inc., Nutley, N.J.

[21] Appl. No.: 717,575

[22] Filed: Jun. 19, 1991

[30] Foreign Application Priority Data

Jul. 10, 1990 [CH] Switzerland .......................... 2304/90

[51] Int. Cl.⁵ ............................................. A61B 10/00
[52] U.S. Cl. ..................................... 206/361; 128/759; 206/363; 206/438; 422/102; 435/296
[58] Field of Search ............... 128/749, 756, 759; 206/205, 209, 210, 229, 361, 363, 364, 438, 514; 215/227, 228, 231, 10; 422/102; 435/296

[56] References Cited

U.S. PATENT DOCUMENTS

| | | | |
|---|---|---|---|
| 3,913,564 | 10/1975 | Freshley | 128/759 |
| 3,939,044 | 2/1976 | Wilkins et al. | 128/759 |
| 3,966,558 | 6/1976 | Calva-Pellicer . | |
| 4,014,748 | 3/1977 | Spinner | 128/759 |
| 4,150,950 | 4/1979 | Takeguchi et al. . | |
| 4,175,008 | 11/1979 | White | 206/569 |
| 4,311,792 | 1/1982 | Avery | 206/569 |
| 4,387,725 | 6/1983 | Mull | 128/759 |
| 4,409,988 | 10/1983 | Greenspan | 128/759 |
| 4,789,639 | 12/1988 | Fleming | 206/569 |
| 4,877,036 | 10/1989 | Saint-Amand | 206/569 |

FOREIGN PATENT DOCUMENTS

328932 8/1989 European Pat. Off. .
330179 7/1958 Switzerland .

*Primary Examiner*—Jimmy G. Foster
*Attorney, Agent, or Firm*—George M. Gould; William H. Epstein; John J. Schlager

[57] ABSTRACT

A transport system for shipping microbiological specimen samples which maintains the life of the bacteria contained in the sample and protects the environment from escape of samples comprises:

(a) a first container provided with removable closure and containing a medium for storing the sample, and
(b) a second container provided with a removable closure cap having an elongate chamber into which one end of a rod disposed therein can be pushed, said rod bearing a swab at its other end, the dimensions of the first and second containers, of the chamber in the closure cap and of the rod carrying the swab being so selected that the first container and a rod inserted therein in the medium and carrying the swab can be contained in the second container closed by the closure cap.

8 Claims, 1 Drawing Sheet

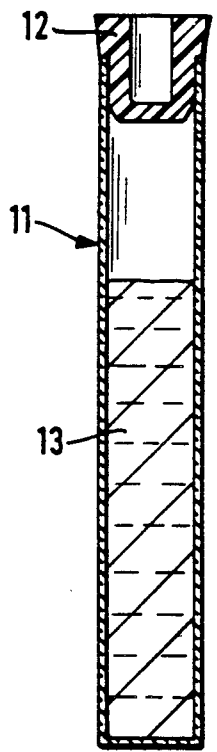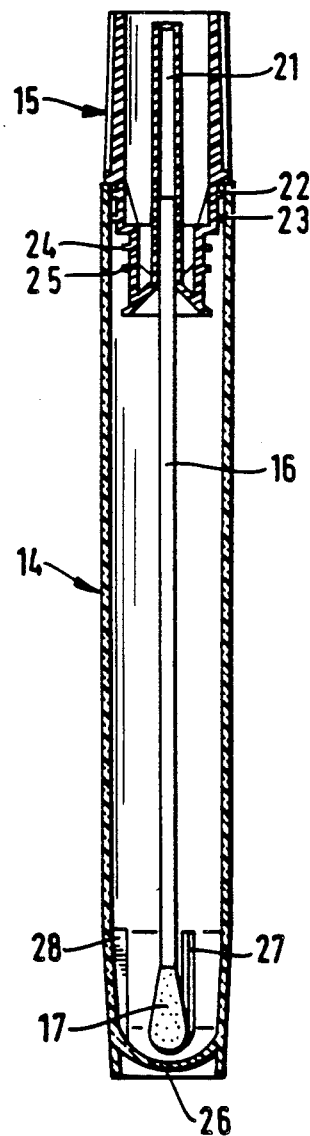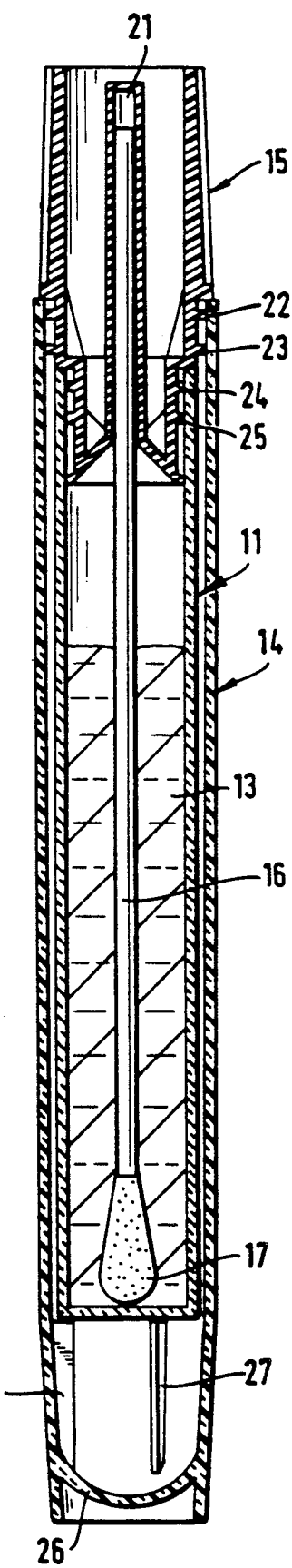

5,096,062

TRANSPORT SYSTEM FOR SHIPPING MICROBIOLOGICAL SAMPLES

BACKGROUND OF THE INVENTION

The invention relates to a transport system for shipping biological samples, more particularly for shipping of samples which are investigated in microbiological diagnosis.

Microbiological samples, e.g. smears, are taken from patients by means of swabs. Such specimens often cannot be processed immediately, either for reasons of space or time, and have to be sent to an investigation laboratory. It is therefore desirable to be able to transfer the specimens to a transport system which reliably complies with the following conditions:

The life of the bacteria contained in the microbiological samples must be maintained. For this purpose they have to be protected, more particularly, from drying out, atmospheric oxygen, and their own toxic metabolic products.

The original biological composition of the samples must be maintained. For example, in the case of mixed cultures, one species must be prevented from growing over another.

The environment must be protected from escape of the specimens during transport. For this purpose it is particularly important to protect the sample container from breakage.

For further processing the samples, the transport system must allow reliable and clean removal of the sample in the investigating laboratory.

A known microorganism transport system is marketed by Merck, Darmstadt, Federal Republic of Germany, under the name Transgerm (Trade Mark). This system consists basically of a small glass tube having a screw closure and containing a medium for the transport of a sample, and a swab packed under sterile conditions. When this system is used, the swab rod has to be broken off after the sample has been taken, so that the swab has a suitable length for insertion into the glass tube and shipment, e.g. by post, in the closed glass tube. To facilitate swab handling, the glass tube screw closure has an elongate cylindrical chamber into which the free end of the swab rod can be pushed after the rod has been broken off. The main disadvantage of this known transport system is that it does not provide any means of protecting the glass tube from breakage. The necessity to break off the swab rod each time makes the use of this system relatively complicated.

The aim of the invention is to provide a transport system which satisfies all the above requirements.

SUMMARY OF THE INVENTION

It is accordingly the object of the invention to solve this problem with a transport system which comprises the following components:

(a) a first container which is provided with a removable closure and which contains a medium for storing the sample, and (b) a second container provided with a removable closure cap which has an elongate chamber into which one end of a rod disposed therein can be pushed, said rod bearing a swab at its other end the dimensions of the first and second containers, of the chamber in the closure cap and of the rod carrying the swab being so selected that the first container and a rod inserted therein in the medium and carrying the the swab can be contained in the second container closed by the closure cap.

The transport system according to the invention particulary provides the following advantages:

(a) After introduction into the transport medium contained in the first container, there is no need to break off the swab rod (as was hitherto necessary in some known transport systems; instead, it slides without any manipulation into the appropriately shaped closure cap of the second container. (b) The second container is used both as a carrier and a packing for the swab (the rod of which is disposed in its closure cap) before it is used, and also as a protective sleeve for the first container during the transport of the sample.

(c) Use of the swab is facilitated by the fact that its rod can remain inserted in the second container closure cap from the very outset and for the entire period of use of the system, i.e. when the smear is taken, during transport to the investigation laboratory, on removal of the swab from the transport system and when the swab is used in the laboratory.

In a preferred embodiment, the closure cap of the second container is so devised that when the closed second container contains the first container and a rod inserted therein in the medium and carrying the swab the closure cap simultaneously closes the first and second container.

The elongate chamber in the closure cap of the second container is approximately cylindrical and preferably has a diameter which decreases slightly in the direction from the open end of the cap to the closed end thereof.

A preferred embodiment of the transport system according to the invention is also characterised in that the first container is made of glass and its closure is a rubber plug or a plastic cap or a foil seal.

Other advantages and features of the present invention will be apparent from the following description of one exemplified embodiment with reference to the accompanying drawings wherein:

BRIEF DESCRIPTION OF THE DRAWINGS

FIG. 1 shows a first container 11 of a transport system according to the invention.

FIG. 2 shows a second container 14 of a transport system according to the invention and a rod 16 with a swab 17 contained in said container.

FIG. 3 shows an enlarged view of an arrangement according to the invention ready for transport and consisting of a first container (shown in FIG. 1) with a rod (16) and swab (17) inserted in a medium (13) therein and a second container 14 (shown in FIG. 2) closed by a closure cap (15).

DETAILED DESCRIPTION OF THE PREFERRED EMBODIMENT

The components of a preferred embodiment of a transport system according to the invention for the shipment of a microbiological sample are shown in detail in true size, i.e., on a 1:1 scale, in FIGS. 1 and 2. A transport system of this kind comprises a first container 11 as shown in FIG. 1 and a second container 14 as shown in FIG. 2. The first container 11 contains a suitable medium 13 for storage of the samples and has a removable closure 12. The second container 14 is preferably made from a suitable plastic and has a removable closure cap 15. This cap has an elongate chamber 21 into which one end of a rod 16 disposed therein can be pushed. At its other end the rod 16 carries a swab 17. The shape and dimensions of the containers 11 and 14, of the bore 21, of the closure cap 15 and of the rod 16 with the swab 17 are so selected that the first container 11 and a rod 16 inserted therein in the meduim 13 and bearing the swab 17 can be contained in the second container 14 closed by the closure cap 15.

The media 13 available at present have a very restricted capability of fixing oxygen. If the second container 14 is gas-permeable, it is therefore necessary to use a first container 11 consisting of a gas-impermeable material in order to prevent oxygen from reaching the bacterium carried by the swab. The first container 11 is therefore preferably made from glass. Basically any other gas-impermeable material, however, is suitable for making the first container 11. For example, it can also be made from gas-impermeable plastic, e.g. acrylodinitrile copolymer. Other gas-impermeable materials, such as metal, ceramic, etc., could also be used, although they would have the disadvantage of being opaque.

If the second container 14 is made from a gas-impermeable material, the first container can be made from a gas-permeable material, e.g. a gas-permeable plastic.

If the medium 13 available has the ability to fix oxygen to such an extent that it can on its own shield the sample from oxygen from ambient air, then both the first container 11 and the second container 14 can be made from a gas-permeable material.

The dimensions of the first container 11 shows in FIG. 1 are, for example, outside diameter: 15 mm, inside diameter: 13 mm, wall thickness: 1 mm, length: 100 mm. By way of example, 8 ml of a suitable medium are placed in the first container 11 so that the level to which the medium 13 is filled in the first container is about 60 mm.

The medium 13 preferably has the following compositon:

|  |  |
| --- | --- |
| NaCl | 5 g/l |
| KH$_2$PO$_4$ | 2 g/l |
| Na-thioglycolate | 1 g/l |
| L-Cysteine HCl | 0.5 g/l |
| Resazurin | 0.002 g/l |
| Potato starch | 5 g/l |
| Agar-agar | 8 g/l |

By way of example, the following media known per se are also suitable as the medium 13:

Transport media according to Amies with and without active carbon (Amies, C. R. "A modified formula of the preparation of Stuart's Transport Medium", Canadian Journal of Public Health, 58,296 (1967), Transport media according to Stuart with and without active carbon (Journal of Pathology and Bacteriology, 58,343 (1946), Transport media according to Cary-Blair (Cary, S. G. and Blair, E. B., "New Transport Medium for Shipment of Clinical Specimens. I. Fecal Specimens", Journal of Bacteriology, 88, 96 (1964).

As shown in FIG. 1, the first container 11 is closed, for example, by a rubber plug 12 before the use of the transport system. Instead of the rubber plug 12, it would also be possible to use a plastic cap with or without a screw closure or a foil seal. The first container is also provided with a transparent label (not shown) which gives the name of the system, the name and address of the manufacturer, storage instructions, expiry date and contents designation, etc., plus a field for patient data.

The second container 14 is perferably made from transparent polystyrene. Polyethylene or polypropylene are also suitable, for example, as materials for the manufacture of the second container.

The diameter of the second container 14 should preferably be such that the first container 11 can without difficulty be inserted in the second container 14 and the walls of the two containers abut except for a narrow gap between them. The diamensions of the second container 14 shown in FIG. 2 are, for example, outside diameter: 19 mm, inside diameter: 16 mm, wall thickness: 1.5 mm, length: 129 mm.

As will be seen from FIG. 2, the bottom end of the second container 14 is of frusto-conical shape. This bottom part of the second container has a set-back round bottom 26 and three spacer ribs. Two of these 27 and 28 are shown in FIG. 2.

The closure cap 15 is made, for example, from dyed polyethylene and has a slightly conical grip portion with grooving and two sealing lips 22, 23 by means of which the cap can be clamped in the second container 14 when the latter is closed. The dimensions of the grip portion 15 are, for example, length: 25 mm, top diameter: 17 mm, bottom diameter: 18 mm. At the bottom end of the cap is a cylinder whose outside diameter of 13 mm corresponds to the inside diameter of the first container. This cylinder also has two sealing lips 24, 25 and an elongate chamber 21 (see FIG. 2) in which the rod 16 of the swab 17 is fitted. The rod 16, for example, has a diameter of 2 mm and a length of 125 mm, rod 16 being pushed into the cap 15 to extent such that the two together approximately have the length of current swabs, i.e. 150 mm.

The rod 16 is perferably made of polypropylene. Wood or any radiation-sterilisable plastic which can be drawn out to form a rod of adequate rigidity is also suitable for the manufacture of the rod 16. The cotton-wool material of the swab 17 may, for example, consist of fatty acid free cotton, cellulose, calcium alginate, polyester of polyterephthalate.

For the intended use, the swab 17 is withdrawn from the second container 14 by removing the cap 15, the specimen is taken from the patient and then the swab 17 together with the samples is pushed into the first container 11 and into the medium 13, preferably until the tip of the swab 17 meets the bottom of the first container 11, so that the entire swab 17 is in any case surrounded by medium 13. When the swab 17 is pushed into the medium 13, the top end of the rod 16 of the swab 17 slides into the chamber 21 in the cap 15 and the latter closes the opening of the first container by means of its bottom inner cylinder. The first container 11 with the swab 17 and the cap 15 are then pushed into the second container 14, thus forming the arrangement shown in FIG. 3. As will be seen from the latter, for transport of the samples the first container 11 and the second container 14 are closed by the closure cap 15. By means of the outer two sealing lips 22, 23 the cap 15 clamps the first container 11 in the second container 14. Unwanted opening of the first container during transport due to the first container 11 dropping from the cap 15 is prevented by the fact that the first container 11 is supported by the three spacer ribs in the bottom part of the second container 14. The resulting transport system protects the first container 11 from breakage and thus prevents the semi-solid contents of this container from escaping due to breakage of said container.

As will be seen from FIG. 3, the dimensions of the first container 11 and of the second container 14, of the chamber 21, of the closure cap 15 and of the rod 16 with the swab 17 are so selected that the first container 11 and a rod 16 inserted in the medium 13 and carrying the swab 17 are contained in the second container 14 closed by the closure cap 15.

The closure cap 15 is preferably such that it can simultaneously close both the first container and the second container as shown in FIG. 3.

As can be seen by comparing the positions of rod 16 in FIGS. 2 and 3, before the swab 17 is used (FIG. 2) and after its introduction into the medium 13, one end of the rod 16 is pushed into the chamber 21 of the closure cap 15 to different distances.

As can be seen from FIG. 3, the chamber 21 of the closure cap 15 preferably has a diameter which decrease slightly in the direction from the open end of the cap to the closed end thereof.

What is claimed is:

1. A transport system for shipping biological samples comprising the following components:
   (a) a first container which is provided with a removable closure and which contains a medium for storing the sample, and
   (b) a second container provided with a removable closure cap which has an elongate chamber into which one end of a rod disposed therein can be pushed, said rod bearing a swab at its other end,
the dimensions of said first and second containers, said chamber in said closure cap and said rod carrying said swab being so selected that said first container and said rod inserted in said medium and carrying said swab can be contained in said second container closed by said closure cap.

2. The transport system of claim 1, wherein said removable closure cap of said second container simultaneously closes said first and second container when said second container contains said first container and said rod inserted in said medium and carrying said swab.

3. The transport system of claim 1, wherein said elongate chamber is approximately cylindrical and has a diameter which decreases slightly in the direction from the open end of said cap to the closed end thereof.

4. The transport system of claim 1, wherein said removable closure of said first container is a rubber plug, a plastic cap, or a foil seal.

5. The transport system of claim 1, wherein said first container is composed of a gas-impermeable material and said second container is composed of a gas-permeable material.

6. The transport system of claim 1, wherein said first container is composed of glass and said second container is composed of a gas-permeable plastic.

7. The transport system of claim 1, wherein said first container is composed of a gas-permeable material and said second container is composed of a gas-impermeable material.

8. The transport system of claim 1, wherein said first container and said second container are each composed of a gas-permeable material and said medium has the capacity for fixing oxygen such that, when said swab is inserted into said medium, the latter shields the sample material carried by said swab from the oxygen contained in the ambient air.

* * * * *